US006844153B2

(12) United States Patent
Waldman et al.

(10) Patent No.: US 6,844,153 B2
(45) Date of Patent: Jan. 18, 2005

(54) COMPOSITIONS AND METHODS FOR IDENTIFYING AND TARGETING CANCER CELLS OF ALIMENTARY CANAL ORIGIN

(75) Inventors: Scott A. Waldman, Ardmore, PA (US); Jason Park, Philadelphia, PA (US); Stephanie Schulz, West Chester, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/819,252

(22) Filed: Mar. 27, 2001

(65) Prior Publication Data

US 2001/0039017 A1 Nov. 8, 2001

Related U.S. Application Data

(60) Provisional application No. 60/192,229, filed on Mar. 27, 2000.

(51) Int. Cl.[7] .................................................. C12Q 1/68
(52) U.S. Cl. ............................................ 435/6; 436/64
(58) Field of Search .............................. 435/6, 7.23, 4; 436/64

(56) References Cited

U.S. PATENT DOCUMENTS

| 5,601,990 A | 2/1997 | Waldman ................... 435/7.23 |
| 5,879,656 A | 3/1999 | Waldman ................... 424/149 |
| 6,130,043 A | 10/2000 | Billing-Medel et al. ....... 435/6 |

FOREIGN PATENT DOCUMENTS

| WO | WO 00/20640 | 4/2000 |

OTHER PUBLICATIONS

Bai et al (Cancer Lett 2002 Feb. 8;176(1):47–55, abstract only).*
Mallo, et al., Int J Cancer, 1997, 74:35–44.*

Iannettoni, M.D. et al., "Detection of Barrett's aenocarcinoma of the gastric cardia with sucrase isomaltase and p53", *Ann. Thorac. Surg.*, 1996, 62, 1460–1466.

Mallo, G.V., et al., "Molecular cloning, sequencing and expression of the MRNA encloding human Cdx1 and Cdx2 homeobox. Down–regulation of Cdx1 and Cdx2 mRNA expression during colorectal carcinogenesis," *Int. J. Cancer (Pred. Oncol)*, 1997, 74, 35–44.

Wu, G.D., et al., "Sucrase–isomaltase gene expression in barrett's esophagus and adenocarcinoma," *Gastroenterology*, 1993, 105, 837–844.

Cagir, B., et al., "Guanylyl cyclase C messenger RNA is a biomarker for recurrent stage II colorectal cancer," *Am. Soc. Internal Med.*, 1999, 131(11), 805–812.

Li,Z., et al., "Peptide–regulated guanylate cyclase pathways in rat colon: in situ localization of GCA, GCC, and guanylin mRNA," *Am. Physiological Soc.*, 1993, G394–G402.

London, R.M., et al., "Signal transduction pathways via guanylin uroguanylin in stomach and intestine," *Am. Physiological Soc.*, 1997, G93–G105.

Mallo, G.V., et al., "Expression of the *Cdx1* and *Cdx2* homeotic genes leads to reduced malignancy in colon cancer–derived cells," *J. Biological Chem.*, 1998, 273(22), 14030–14036.

* cited by examiner

*Primary Examiner*—Larry R. Helms
*Assistant Examiner*—Misook Yu
(74) *Attorney, Agent, or Firm*—Cozen O'Connor, P.C.

(57) ABSTRACT

Screening and diagnostic reagents, kits and methods for metastatic colorectal cancer or primary and/or metastatic stomach or esophageal cancer are disclosed. Vaccines compositions and methods of for treating and preventing metastatic colorectal cancer or primary and/or metastatic stomach or esophageal cancer are disclosed.

8 Claims, No Drawings

SEQUENCE LISTING

<160> NUMBER OF SEQ ID NOS: 2

<210> SEQ ID NO 1
<211> LENGTH: 1745
<212> TYPE: DNA
<213> ORGANISM: Homo sapiens

<400> SEQUENCE: 1

```
gcgcccctgg cagccttcaa cgtcggtccc caggcagcat ggtgaggtct gctcccggac      60
cctcgccacc atgtacgtga gctacctcct ggacaaggac gtgagcatgt accctagctc     120
cgtgcgccac tctggcggcc tcaacctggc gccgcagaac ttcgtcagcc ccccgcagta     180
cccggactac ggcggttacc acgtggcggc cgcagctgca gcgcagaact tggacagcgc     240
gcagtccccg gggccatcct ggccggcagc gtatggcgcc ccactccggg aggactggaa     300
tggctacgcg cccggaggcg cggccgccgc caacgccgtg gctcacgcgc tcaacggtgg     360
ctccccggcc gcagccatgg gctacagcag ccccgcagac taccatccgc accaccaccc     420
gcatcaccac ccgcaccacc cggccgccgc gccttcctgc gcttctgggc tgctgcaaac     480
gctcaacccc ggccctcctg ggcccgccgc caccgctgcc gccgagcagc tgtctcccgg     540
```

-continued

```
cggccagcgg cggaacctgt gcgagtggat gcggaagccg gcgcagcagt ccctcggcag     600
ccaagtgaaa accaggacga agacaaata tcgagtggtg tacacggacc accagcggct      660
ggagctggag aaggagtttc actacagtcg ctacatcacc atccggagga aagccgagct     720
agccgccacg ctgggctct ctgagaggca ggttaaaatc tggtttcaga accgcagagc      780
aaaggagagg aaaatcaaca agaagaagtt gcagcagcaa cagcagcagc agccaccaca    840
gccgcctccg ccgccaccac agcctcccca gcctcagcca ggtcctctga aagtgtccc     900
agagcccttg agtccggtgt cttccctgca agcctcagtg tctggctctg tccctggggt   960
tctggggcca actgggggg tgctaaaccc caccgtcacc cagtgaccca ccggggtctg    1020
cagcggcaga gcaattccag gctgagccat gaggagcgtg gactctgcta gactcctcag  1080
gagagacccc tccctccca cccacagcca tagacctaca gacctggctc tcagaggaaa    1140
aatgggagcc aggagtaaga caagtgggat ttggggcctc aagaaatata ctctcccaga   1200
tttttacttt ttccatctgg cttttttctgc cactgaggag acagaaagcc tccgctgggc  1260
ttcattccgg actggcagaa gcattgcctg gactgaccac accaaccagc ttcatctatc   1320
cgactcttct cttcctagat ctgcaggctg cacctctggc tagagccgag gggagagagg  1380
gactcaaggg aaaggcaagc ttgaggccaa gatggctgct gcctgctcat ggccctcgga  1440
ggtccagctg ggcctcctgc ctccgggcag caaggtttac actgcggaac gcaaaggcag  1500
ctaagataga aagctggact gaccaaagac tgcagaaccc ccaggtgccc ctgcgtcttt   1560
tttctcttcc ctttcccaga ccaggaaagg cttggctggt gtatgcacag ggtgtggtat    1620
gaggggggtgg ttattggact ccaggcctga ccaggggggcc cgaacaggac ttgttagaga  1680
gcctgtcacc agagcttctc tgggctgaat gtatgtcagt gctataaatg ccagagccaa   1740
cctgg                                                                    1745
```

<210> SEQ ID NO 2
<211> LENGTH: 311
<212> TYPE: PRT
<213> ORGANISM: Homo sapiens

<400> SEQUENCE: 2

```
Met Tyr Val Ser Tyr Leu Leu Asp Lys Asp Val Ser Met Tyr Pro Ser
1               5                   10                  15

Ser Val Arg His Ser Gly Gly Leu Asn Leu Ala Pro Gln Asn Phe Val
            20                  25                  30

Ser Pro Pro Gln Tyr Pro Asp Tyr Gly Gly Tyr His Val Ala Ala Ala
        35                  40                  45

Ala Ala Ala Gln Asn Leu Asp Ser Ala Gln Ser Pro Gly Pro Ser Trp
    50                  55                  60

Pro Ala Ala Tyr Gly Ala Pro Leu Arg Glu Asp Trp Asn Gly Tyr Ala
65                  70                  75                  80

Pro Gly Gly Ala Ala Ala Ala Asn Ala Val Ala His Ala Leu Asn Gly
                85                  90                  95

Gly Ser Pro Ala Ala Met Gly Tyr Ser Ser Pro Ala Asp Tyr His
            100                 105                 110

Pro His His His Pro His His Pro His His Pro Ala Ala Ala Pro
        115                 120                 125

Ser Cys Ala Ser Gly Leu Leu Gln Thr Leu Asn Pro Gly Pro Pro Gly
    130                 135                 140

Pro Ala Ala Thr Ala Ala Ala Glu Gln Leu Ser Pro Gly Gly Gln Arg
```

-continued

```
145                 150                 155                 160
Arg Asn Leu Cys Glu Trp Met Arg Lys Pro Ala Gln Gln Ser Leu Gly
                165                 170                 175

Ser Gln Val Lys Thr Arg Thr Lys Asp Lys Tyr Arg Val Val Tyr Thr
            180                 185                 190

Asp His Gln Arg Leu Glu Leu Glu Lys Glu Phe His Tyr Ser Arg Tyr
        195                 200                 205

Ile Thr Ile Arg Arg Lys Ala Glu Leu Ala Ala Thr Leu Gly Leu Ser
    210                 215                 220

Glu Arg Gln Val Lys Ile Trp Phe Gln Asn Arg Arg Ala Lys Glu Arg
225             230                 235                 240

Lys Ile Asn Lys Lys Lys Leu Gln Gln Gln Gln Gln Gln Gln Pro Pro
            245                 250                 255

Gln Pro Pro Pro Pro Pro Gln Pro Pro Gln Pro Gln Pro Gly Pro
            260                 265                 270

Leu Arg Ser Val Pro Glu Pro Leu Ser Pro Val Ser Ser Leu Gln Ala
        275                 280                 285

Ser Val Ser Gly Ser Val Pro Gly Val Leu Gly Pro Thr Gly Gly Val
    290                 295                 300

Leu Asn Pro Thr Val Thr Gln
305                 310
```

US 6,844,153 B2

COMPOSITIONS AND METHODS FOR IDENTIFYING AND TARGETING CANCER CELLS OF ALIMENTARY CANAL ORIGIN

CROSS REFERENCE TO RELATED PATENT APPLICATIONS

This application claims priority to U.S. Provisional Application No. 60/192,229 filed Mar. 27, 2000, which is incorporated herein by reference.

FIELD OF THE INVENTION

The present invention relates to in vitro diagnostic methods for detecting cancer cells of the alimentary canal, particularly primary and metastatic stomach and esophageal cancer and metastatic colorectal cancer, and to kits and reagents for performing such methods. The present invention relates to compounds and methods for in vivo imaging and treatment of tumors originating from the alimentary canal, particularly primary and metastatic stomach and esophageal tumors and metastatic colorectal tumors. The present invention relates to methods and compositions for making and using targeted gene therapy, antisense and drug compositions. The present invention relates to prophylactic and therapeutic vaccines against cancer cells of the alimentary canal, particularly primary and metastatic stomach and esophageal cancer and metastatic colorectal cancer and compositions and methods of making and using the same.

BACKGROUND OF THE INVENTION

U.S. Pat. No. 5,518,888, issued May 12, 1996, U.S. Pat. No. 5,601,990, issued Feb. 11, 1997, U.S. Pat. No. 6,060,037 issued Apr. 26, 2000, U S. Pat. No. 5,962,2200, issued Oct. 5, 1999, and U.S. Pat. No. 5,879,656 issued May 9, 1999, are each incorporated herein by reference and U.S. patent application Ser. No. 09/180,237 filed Mar. 12, 1997, is incorporated herein by reference.

There is a need for reagents, kits and methods for screening, diagnosing and monitoring individuals with cancer originating from the alimentary canal, particularly primary and metastatic stomach and esophageal cancer and metastatic colorectal cancer. There is a need for reagents, kits and methods for identifying and confirming that a cancer of unknown origin is originating from the alimentary canal and for analyzing tissue and cancer samples to identify and confirm cancer originating from the alimentary canal and to determine the level of migration of such cancer cells. There is a need for compositions which can specifically target colorectal, stomach and esophageal cancer cells. There is a need for imaging agents which can specifically bind to colorectal, stomach and esophageal cancer cells. There is a need for improved methods of imaging colorectal, stomach and esophageal cancer cells. There is a need for therapeutic agents which can specifically bind to colorectal, stomach and esophageal cancer cells. There is a need for improved methods of treating individuals who are suspected of suffering from primary and/or metastatic stomach or esophageal cancer or metastatic colorectal cancer. There is a need for vaccine composition to treat colorectal, stomach and esophageal cancer. There is a need for vaccine composition to treat and prevent metastasized colorectal, stomach and esophageal cancer. There is a need for therapeutic agents which can specifically deliver gene therapeutics, antisense compounds and other drugs to colorectal, stomach and esophageal cancer cells.

SUMMARY OF THE INVENTION

The invention further relates to in vitro methods of determining whether or not an individual has cancer originating from the alimentary canal, particularly primary and metastatic stomach and esophageal cancer and metastatic colorectal cancer. The present invention relates to in vitro methods of examining samples of non-colorectal tissue and body fluids from an individual to determine whether or not CDX2, which is expressed by normal colon cells and by colorectal, stomach and esophageal tumor cells, is being expressed by cells in samples other than colon. The presence of CDX2 protein or of the CDX2 gene transcript in samples outside the colorectal track is indicative of expression of CDX2 and is evidence that the individual may be suffering from metastasized colon cancer or primary or metastatic stomach and/or esophageal cancer. In patients suspected of suffering from colorectal cancer, the presence of CDX2 protein or of the CDX2 gene transcript in samples outside the colorectal track is supportive of the conclusion that the individual is suffering from metastatic colorectal cancer. The diagnosis of metastatic colorectal cancer may be made or confirmed. In patients suspected of suffering from stomach or esophageal cancer, the presence of CDX2 protein or of the CDX2 gene transcript in samples outside the colorectal track is supportive of the conclusion that the individual is suffering from primary and/or metastatic stomach or esophageal cancer. The diagnosis of primary and/or metastatic stomach or esophageal cancer may be made or confirmed.

The invention further relates to in vitro methods of determining whether or not tumor cells are colorectal, stomach or esophageal in origin. The present invention relates to in vitro methods of diagnosing whether or not an individual suffering from cancer is suffering from colorectal, stomach or esophageal cancer. The present invention relates to in vitro methods of examining samples of tumors from an individual to determine whether or not CDX2 protein, which is expressed by colorectal, stomach or esophageal tumor cells, is being expressed by the tumor cells. The presence of a CDX2 protein or of the CDX2 gene transcript is indicative of expression of CDX2 and evidence that the individual may be suffering from colorectal, stomach or esophageal cancer. In tumors which are suspected of being colorectal, stomach or esophageal tumors, the presence of a CDX2 protein or of the CDX2 gene transcript supports the conclusion that the tumors are of colorectal, stomach or esophageal cancer and the diagnosis of colorectal, stomach or esophageal cancer.

The invention further relates to in vitro kits for practicing the methods of the invention and to reagents and compositions useful as components in such in vitro kits of the invention.

The invention further relates to a method of imaging primary and metastatic stomach and esophageal tumors and metastatic colorectal tumors and to methods of treating an individual suspected of suffering from primary and metastatic stomach and esophageal tumors and metastatic colorectal tumors comprising the steps of administering to said individual a pharmaceutical compositions according to the invention, wherein the compositions or conjugated compounds are present in an amount effective for therapeutic or diagnostic use in humans suffering from primary and/or metastatic stomach or esophageal tumors and metastatic colorectal tumors cancer.

The invention further relates to a method of delivering an active agent to primary and metastatic stomach and esophageal tumor cells and metastatic colorectal tumors cells comprising the steps of administering to an individual who has primary and/or metastatic stomach or esophageal tumors or metastatic colorectal cancer, a pharmaceutical composition comprising a pharmaceutically acceptable carrier or diluent, and an unconjugated compositions that comprises a liposome that includes CDX2 ligands on its surface and an active component encapsulated therein.

The invention further relates to killed or inactivated colorectal, stomach or esophageal tumor cells that comprise a protein comprising at least one epitope of a CDX2 protein; and to vaccines comprising the same. In some embodiments, the killed or inactivated cells or particles comprise a CDX2 protein. In some embodiments, the killed or inactivated cells or particles are haptenized.

The invention further relates to methods of treating individuals suffering from colorectal, stomach or esophageal cancer and to methods of treating individuals susceptible colorectal, stomach or esophageal cancer. The method of the present invention provides administering to such individuals an effective amount of such vaccines. The invention further relates to the use of such vaccines as immunotherapeutics.

DESCRIPTION OF PREFERRED EMBODIMENTS

Definitions

As used herein, the term "CDX2" is meant to refer to the cellular protein expressed by normal colorectal cells, as well as primary and metastasized colorectal, stomach and esophageal cancer cells. In normal individuals, CDX2 is found exclusively in cells of intestine, in particular in cells in the duodenum, small intestine (jejunum and ileum), the large intestine, colon (cecum, ascending colon, transverse colon, descending colon and sigmoid colon) and rectum.

As used herein, the term "functional fragment" as used in the term "functional fragment of a CDX2 gene transcript" is meant to refer to fragments of CDX2 gene transcript which are functional with respect to nucleic acid molecules with full length sequences. For example, a functional fragment may be useful as an oligonucleotide or nucleic acid probe, a primer, an antisense oligonucleotide or nucleic acid molecule or a coding sequence. The nucleotide sequence encoding human CDX2 protein is disclosed in Mallo, G. V. et al. 1991 *Intl. J. Cancer* 74(1):35–44 and GenBank Accession No. U51096, which are both incorporated herein by reference.

As used herein, the term "functional fragment" as used in the term "functional fragment of a CDX2 protein" is meant to fragments of CDX2 protein which function in the same manner as CDX2 protein with full length sequences. For example, an immunogenically functional fragment of a CDX2 protein comprises an epitope recognized by an anti-CDX2 antibody. A ligand-binding functional fragment of CDX2 comprises a sequence which forms a structure that can bind to a ligand which recognizes and binds to CDX2 protein.

As used herein, the term "epitope recognized by an anti-CDX2 protein antibody" refers to those epitopes specifically recognized by an anti-CDX2 protein antibody.

As used herein, the term "antibody" is meant to refer to complete, intact antibodies, and Fab fragments and F(ab)$_2$ fragments thereof. Complete, intact antibodies include monoclonal antibodies such as murine monoclonal antibodies, chimeric antibodies and humanized antibodies.

As used herein, the term "CDX2 ligand" is meant to refer to compounds which specifically bind to a CDX2 protein. Antibodies that bind to CDX2 are CDX2 ligands. A CDX2 ligand may be a protein, peptide or a non-peptide.

As used herein, the term "active agent" is meant to refer to compounds that are therapeutic agents or imaging agents.

As used herein, the term "radiostable" is meant to refer to compounds which do not undergo radioactive decay; i.e. compounds which are not radioactive.

As used herein, the term "therapeutic agent" is meant to refer to chemotherapeutics, toxins, radiotherapeutics, targeting agents or radiosensitizing agents.

As used herein, the term "chemotherapeutic" is meant to refer to compounds that, when contacted with and/or incorporated into a cell, produce an effect on the cell including causing the death of the cell, inhibiting cell division or inducing differentiation.

As used herein, the term "toxin" is meant to refer to compounds that, when contacted with and/or incorporated into a cell, produce the death of the cell.

As used herein, the term "radiotherapeutic" is meant to refer to radionuclides which when contacted with and/or incorporated into a cell, produce the death of the cell.

As used herein, the term "targeting agent" is meant to refer compounds which can be bound by and or react with other compounds. Targeting agents may be used to deliver chemotherapeutics, toxins, enzymes, radiotherapeutics, antibodies or imaging agents to cells that have targeting agents associated with them and/or to convert or otherwise transform or enhance co-administered active agents. A targeting agent may include a moiety that constitutes a first agent that is localized to the cell which when contacted with a second agent either is converted to a third agent which has a desired activity or causes the conversion of the second agent into an agent with a desired activity. The result is the localized agent facilitates exposure of an agent with a desired activity to the cancer cell.

As used herein, the term "radiosensitizing agent" is meant to refer to agents which increase the susceptibility of cells to the damaging effects of ionizing radiation. A radiosensitizing agent permits lower doses of radiation to be administered and still provide a therapeutically effective dose.

As used herein, the term "imaging agent" is meant to refer to compounds which can be detected.

As used herein, the term "CDX2 binding moiety" is meant to refer to the portion of a conjugated compound that constitutes an CDX2 ligand.

As used herein, the term "active moiety" is meant to refer to the portion of a conjugated compound that constitutes an active agent.

As used herein, the terms "conjugated compound" and "conjugated composition" are used interchangeably and meant to refer to a compound which comprises a CDX2 binding moiety and an active moiety and which is capable of binding to CDX2. Conjugated compounds according to the present invention comprise a portion which constitutes an CDX2 ligand and a portion which constitutes an active agent. Thus, conjugated compounds according to the present invention are capable of specifically binding to the CDX2 and include a portion which is a therapeutic agent or imaging agent. Conjugated compositions may comprise crosslinkers and/or molecules that serve as spacers between the moieties.

As used herein, the terms "crosslinker", "crosslinking agent", "conjugating agent", "coupling agent", "condensation reagent" and "bifunctional crosslinker" are used interchangeably and are meant to refer to molecular groups which are used to attach the CDX2 ligand and the active agent to thus form the conjugated compound.

As used herein, the term "colorectal cancer" is meant to include the well-accepted medical definition that defines colorectal cancer as a medical condition characterized by cancer of cells of the intestinal tract below the small intestine (i.e. the large intestine (colon), including the cecum, ascending colon, transverse colon, descending colon, and sigmoid colon, and rectum). Additionally, as used herein, the term "colorectal cancer" is meant to further include medical conditions which are characterized by cancer of cells of the duodenum and small intestine (jejunum and ileum). The definition of colorectal cancer used herein is more expansive than the common medical definition but is provided as such since the cells of the duodenum and small intestine also contain CDX2.

As used herein, the term "stomach cancer" is meant to include the well-accepted medical definition that defines stomach cancer as a medical condition characterized by cancer of cells of the stomach.

As used herein, the term "esophageal cancer" is meant to include the well-accepted medical definition that defines esophageal cancer as a medical condition characterized by cancer of cells of the esophagus.

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body.

As used herein, the term "metastasized colorectal cancer cells" is meant to refer to colorectal cancer cells which have metastasized. Metastasized colorectal cancer cells localized in a part of the body other than the duodenum, small intestine (jejunum and ileum), large intestine (colon), including the cecum, ascending colon, transverse colon, descending colon, and sigmoid colon, and rectum.

As used herein, the term "metastasized stomach cancer cells" is meant to refer to stomach cancer cells which have metastasized. Metastasized stomach cancer cells localized in a part of the body other than the stomach.

As used herein, the term "metastasized esophageal cancer cells" is is meant to refer to colorectal cancer cells which have metastasized. Metastasized esophageal cancer cells localized in a part of the body other than the esophagus.

As used herein, the term "non-colorectal sample" and "extra-intestinal sample" are used interchangeably and meant to refer to a sample of tissue or body fluid from a source other than colorectal tissue. In some preferred embodiments, the non-colorectal sample is a sample of tissue such as lymph nodes. In some preferred embodiments, the non-colorectal sample is a sample of extra-intestinal tissue which is an adenocarcinoma of unconfirmed origin. In some preferred embodiments, the non-colorectal sample is a blood sample.

As used herein, "an individual suffering from an adenocarcinoma of unconfirmed origin" is meant to refer to an individual who has a tumor in which the origin has not been definitively identified.

As used herein, "an individual is suspected of being susceptible to colorectal, stomach or esophageal cancer" is meant to refer to an individual who is at a particular risk of developing colorectal, stomach or esophageal cancer. Examples of individuals at a particular risk of developing colorectal, stomach or esophageal cancer are those whose family medical history indicates above average incidence of colorectal, stomach or esophageal cancer among family members and/or those who have already developed colorectal, stomach or esophageal cancer and have been effectively treated who therefore face a risk of relapse and recurrence.

As used herein, the term "antisense composition" and "antisense molecules" are used interchangeably and are meant to refer to compounds that regulate transcription or translation by hybridizing to DNA or RNA and inhibiting and/or preventing transcription or translation from taking place. Antisense molecules include nucleic acid molecules and derivatives and analogs thereof. Antisense molecules hybridize to DNA or RNA in the same manner as complementary nucleotide sequences do regardless of whether or not the antisense molecule is a nucleic acid molecule or a derivative or analog. Antisense molecules may inhibit or prevent transcription or translation of genes whose expression is linked to cancer.

As used herein, the term "CDX2 immunogen" is meant to refer to CDX2 protein or a fragment thereof or a protein that comprises the same or a haptenized product thereof, cells and particles which display at least one CDX2 epitope, and haptenized cells and haptenized particles which display at least one CDX2 epitope.

As used herein, the term "recombinant expression vector" is meant to refer to a plasmid, phage, viral particle or other vector which, when introduced into an appropriate host, contains the necessary genetic elements to direct expression of the coding sequence that encodes the protein. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences.

As used herein, the term "illegitimate transcription" is meant to refer to the low level or background expression of tissue-specific genes in cells from other tissues. The phenomenon of illegitimate transcription thus provides copies of mRNA for a tissue specific transcript in other tissues. If detection techniques used to detect gene expression are sufficiently sensitive to detect illegitimate transcription, the expression level of the transcript in negative samples due to illegitimate transcription must be discounted using controls and/or quantitative assays and/or other means to eliminate the incidence of false positive due to illegitimate transcription. Alternatively, detection of evidence of CDX2 gene expression in sample is achieved without detecting CDX2 gene transcript present due to illegitimate transcription. This is accomplished using techniques which are not sufficiently sensitive to detect the CDX2 gene transcript present due to illegitimate transcription which is present as background.

CDX2

Carcinomas derived from the colorectal cells, stomach or esophagus express CDX2. The expression of CDX2 by such tumors enables this protein and its mRNA to be a specific biomarker for the presence of cancer cells in extra-intestinal tissues and blood. Indeed, this characteristic permits the detection of CDX2 mRNA by RT-PCR analysis to be a diagnostic test to stage patients with colorectal, stomach or esophageal cancer and follow patients after surgery for evidence of recurrent disease in their blood as well as to detect colorectal, stomach and esophageal cancers. Further, the CDX2 may be targeted with a ligand conjugated to an active agent in order to deliver the active agent to tumor cells in vivo.

U.S. Pat. No. 5,518,888 issued May 21, 1996 to Waldman, PCT application PCT/US94/12232 filed Oc. 26, 1994, U.S. application Ser. No. 08/467,920 filed Jun. 6, 1995, and U.S. application Ser. No. 08/583,447 filed Jan. 5, 1996, which are each incorporated herein by reference, disclose that metastasized colorectal tumors can be targeted for delivery of active compounds by targeting ST receptors (also referred to as guanylin cyclase C or GCC). The presence of ST receptors on cells outside of the intestinal tract as a marker for colorectal cancer allows for the screening, identification and treatment of individuals with metastasized colorectal tumors. ST receptors may also be used to target delivery of gene therapeutics and antisense compounds to colorectal cells.

U.S. Pat. No. 5,601,990 issued Feb. 11, 1997 to Waldman, PCT application No. PCT/US94/12232 filed Oct. 26, 1994, and PCT application No. PCT/US97/07467 filed May 2, 1997, which are each incorporated herein by reference, disclose that detection of evidence of expression of ST receptors in samples of tissue and body fluid from outside the intestinal track indicate metastasized colorectal cancer.

PCT application PCT/US97/07565 filed May 2, 1997, which is incorporated herein by reference, disclose that immunogens with epitopes that can be targeted by antibodies that react with ST receptors can be used in vaccines compositions useful as prophylactic and therapeutic anti-metastatic colorectal cancer compositions.

It has been discovered that in addition to normal colon cells, primary and metastasized colon, stomach and esophageal carcinoma cells express CDX2. Normal stomach and esophageal cells do not express CDX2. Thus, the present invention provides the use of CDX2 as a specific molecular diagnostic marker for the diagnosis, staging, and post-operative surveillance of patients with metastasized colon cancer and primary and metastasized stomach and esophageal cancer.

Detection of the expression of CDX2 employing molecular techniques, including, but not limited to, RT-PCR, can be employed to diagnose and stage patients, follow the development of recurrence after surgery and/or remission, and, potentially, screen normal people for the development of colorectal, stomach or esophageal cancer.

The amino acid of the CDX2 protein and the nucleotide sequence of the CDX2 gene transcript is set forth in Mallo, G. V. et al. 1991 *Intl. J. Cancer* 74(1):35–44 and GenBank Accession No. U51096, which are both incorporated herein by reference.

CDX2 is unique in that it is only expressed in normal intestinal cells. Mucosal cells lining the intestine are joined together by tight junctions which form a barrier against the passage of intestinal contents into the blood stream and components of the blood stream into the intestinal lumen. Therefore, the apical location of cells expressing CDX2 results in the isolation of such cells from the circulatory system so that they may be considered to exist separate from the rest of the body; essentially the "outside" of the body. Therefore, the rest of the body is considered "outside" the intestinal tract. Compositions administered "outside" the intestinal tract are maintained apart and segregated from the only cells which normally express CDX2. Conversely, tissue samples taken from tissue outside of the intestinal tract do not normally contain cells which express CDX2.

In individuals suffering from colorectal cancer, the cancer cells are often derived from cells that produce and display the CDX2 and these cancer cells continue to produce CDX2. It has been observed that CDX2 is expressed by colorectal cancer cells. Likewise, CDX2 is expressed by stomach and esophageal cancer cells.

The expression of CDX2 by colorectal tumor cells provides a detectable target for in vitro screening, monitoring and staging as well as a target for in vivo delivery of conjugated compositions that comprise active agents for the imaging and treatment. CDX2 can also serve as targets for vaccines which may be used to protect against metastasized colorectal cancer or to treat individiuals with metastasized colorectal cancer.

The expression of CDX2 by stomach and esophageal tumor cells provides a detectable target for in vitro screening, monitoring and staging as well as a target for in vivo delivery of conjugated compositions that comprise active agents for the imaging and treatment. CDX2 can also serve as targets for vaccines which may be used to protect against primary and metastatic stomach and esophageal cancer or to treat individiuals with primary and metastatic stomach and esophageal cancer.

In Vitro Diagnostics

According to some embodiments of the invention, compositions, kits and in vitro methods are provided for screening, diagnosing and analyzing patients and patient samples to detect evidence of CDX2 expression by cells outside of the intestinal tract wherein the expression of CDX2 may be suggestive of metastasized colorectal cancer or primary or metastatic stomach or esophageal cancer. In patients suspected of having metastasized colorectal cancer or primary or metastatic stomach or esophageal cancer evidence of CDX2 expression by cells outside of the intestinal tract is indicative of metastasized colorectal cancer or primary or metastatic stomach or esophageal cancer and can be used in the diagnosis, monitoring and staging of such patients. Furthermore, the present invention relates to methods, compositions and kits useful in the in vitro screening, and analysis of patient and patient samples to detect evidence of CDX2 expression by tumor cells outside of the intestinal tract wherein the presence of cells that express CDX2 suggests or confirms that a tumor is of colorectal or stomach or esophageal cancer origin. In an additional aspect of the invention, compositions, kits and methods are provided which are useful to visualize metastasized colorectal cancer or primary or metastatic stomach or esophageal cancer cells.

In vitro screening and diagnostic compositions, methods and kits can be used in the monitoring of individuals who are in high risk groups for colorectal, stomach or esophageal cancer such as those who have been diagnosed with localized disease and/or metastasized disease and/or those who are genetically linked to the disease. In vitro screening and diagnostic compositions, methods and kits can be used in the monitoring of individuals who are undergoing and/or have been treated for primary colorectal, stomach or esophageal cancer to determine if the cancer has metastasized. In vitro screening and diagnostic compositions, methods and kits can be used in the monitoring of individuals who are undergoing and/or have been treated for colorectal, stomach or esophageal cancer to determine if the cancer has been eliminated. In vitro screening and diagnostic compositions, methods and kits can be used in the monitoring of individuals who are otherwise susceptible, i.e. individuals who have been identified as genetically predisposed such as by genetic screening and/or family histories. Advancements in the understanding of genetics and developments in technology as well as epidemiology allow for the determination of probability and risk assessment an individual has for developing stomach or esophageal cancer. Using family health histories and/or genetic screening, it is possible to estimate the probability that a particular individual has for developing certain types of cancer including colorectal, stomach or esophageal cancer. Those individuals that have been identified as being predisposed to developing a particular form of cancer can be monitored or screened to detect evidence of colorectal, stomach or esophageal cancer. Upon discovery of such evidence, early treatment can be undertaken to combat the disease. Accordingly, individuals who are at risk for developing colorectal, stomach or esophageal cancer may be identified and samples may be isolated form such individuals. The invention is particularly useful for monitoring individuals who have been identified as having family medical histories which include relatives who have suffered from colorectal, stomach or esophageal cancer. Likewise, the invention is particularly useful to monitor individuals who have been diagnosed as having colorectal, stomach or esophageal cancer and, particularly those who have been treated and had tumors removed and/or are otherwise experiencing remission including those who have been treated for colorectal, stomach or esophageal cancer.

In vitro screening and diagnostic compositions, methods and kits can be used in the analysis of tumors. Expression of CDX2 is a marker for cell type and suggests the origin of adenocarcinoma of unconfirmed origin may be colorectal, stomach or esophageal tumors. Detection of CDX2 expression can also be used to assist in an initial diagnosis of colorectal, stomach or esophageal cancer or to confirm such diagnosis. Tumors believed to be colorectal, stomach or esophageal in origin can be confirmed as such using the compositions, methods and kits of the invention.

In vitro screening and diagnostic compositions, kits and methods of the invention can be used to analyze tissue samples from the stomach or esophagus to identify primary stomach or esophageal cancer.

In vitro screening and diagnostic compositions, kits and methods of the invention can be used to analyze tissue samples from the colon to detect the amount of invasion by primary colorectal cancer into the intestinal tissue.

According to the invention, compounds are provided which bind to CDX2 gene transcript or protein. Normal tissue in the body does not have CDX2 transcript or protein except cells of the intestinal tract. The expression of CDX2 is a marker for cell type and is useful in the identification of colorectal, stomach or esophageal cancer in extra-intestinal samples.

In some embodiments of the invention, non-colorectal tissue and fluid samples or tumor samples may be screened to identify the presence or absence of CDX2 protein. Techniques such as ELISA assays and Western blots may be performed to determine whether CDX2 is present in a sample.

In some embodiments of the invention, non-colorectal tissue and fluid samples or tumor samples may be screened to identify whether CDX2 are being expressed in cells outside of the colorectal tract by detecting the presence or absence of CDX2 gene transcript. The presence of CDX2 gene transcript or cDNA generated therefrom can be determined using techniques such as PCR amplification, branched oligonucleotide technology, Northern Blots (mRNA), Southern Blots (cDNA), or oligonucleotide hybridization.

In some embodiments of the invention, cells of non-colorectal tissue samples or tumor samples may be examined to identify the presence or absence of CDX2 proteins. Techniques such as immunohistochemistry blots may be performed on tissue sections to determine whether CDX2 are present in a sample.

In some embodiments of the invention, cells of non-colorectal tissue samples or tumor samples may be examined to determine whether CDX2 are being expressed in cells outside of the colorectal tract by detecting the presence or absence of the CDX2 gene transcript. The presence of the CDX2 gene transcript or cDNA generated therefrom in cells from tissue sections can be determined using techniques such as in situ hybridization.

The presence of CDX2 in non-colorectal tissue and fluid samples or on cells from non-colorectal tissue samples suggests possible stomach or esophageal cancer. The presence of CDX2 in a tumor sample or on tumor cells suggests that the tumor may be colorectal, stomach or esophageal in origin. The presence of the CDX2 gene transcript in non-colorectal tissue and fluid samples or in cells from non-colorectal tissue samples suggests possible colorectal, stomach or esophageal cancer. The presence of the CDX2 gene transcript in tumor samples and tumor cells suggests that the tumor may be colorectal, stomach or esophageal in origin.

Samples may be obtained from resected tissue or biopsy material including needle biopsy. Tissue section preparation for surgical pathology may be frozen and prepared using standard techniques. Immunohistochemistry and in situ hybridization binding assays on tissue sections are performed in fixed cells. Extra-intestinal samples may be homogenized by standard techniques such as sonication, mechanical disruption or chemical lysis such as detergent lysis. It is also contemplated that tumor samples in body fluids such as blood, urine, lymph fluid, cerebral spinal fluid, amniotic fluid, vaginal fluid, semen and stool samples may also be screened to determine if such tumors are colorectal, stomach or espophageal in origin.

Non-colorectal tissue samples may be obtained from any tissue except those of the colorectal tract, i.e. the intestinal tract below the small intestine (i.e. the large intestine (colon), including the cecum, ascending colon, transverse colon, descending colon, and sigmoid colon, and rectum) and additionally the duodenum and small intestine (jejunum and ileum). The normal cells of all tissue except those of the colorectal tract do not express CDX2. Thus if CDX2 protein or the CDX2 gene transcript are detected in non-colorectal samples, the possible presence of colorectal, stomach or esophageal cancer cells is suggested. In some preferred embodiments, the tissue samples are lymph nodes.

Tissue samples may be obtained by standard surgical techniques including use of biopsy needles. One skilled in the art would readily appreciate the variety of test samples that may be examined for CDX2 and recognize methods of obtaining tissue samples.

Tissue samples may be homogenized or otherwise prepared for screening for the presence of CDX2 by well known techniques such as sonication, mechanical disruption, chemical lysis such as detergent lysis or combinations thereof.

Examples of body fluid samples include blood, urine, lymph fluid, cerebral spinal fluid, amniotic fluid, vaginal fluid and semen. In some preferred embodiments, blood is used as a sample of body fluid. Cells may be isolated from fluid sample such as centrifugation. One skilled in the art would readily appreciate the variety of test samples that may be examined for CDX2. Test samples may be obtained by such methods as withdrawing fluid with a syringe or by a swab. One skilled in the art would readily recognize other methods of obtaining test samples.

In an assay using a blood sample, the blood plasma may be separated from the blood cells. The blood plasma may be screened for CDX2 including truncated proteins which are released into the blood when one or more CDX2 are cleaved from or sloughed off from tumor cells. In some embodiments, blood cell fractions are screened for the presence of colorectal, stomach or esophageal tumor cells. In some embodiments, lymphocytes present in the blood cell fraction are screened by lysing the cells and detecting the presence of CDX2 protein or the CDX2 gene transcript which may be present as a result of the presence of any stomach or esophageal tumor cells that may have been engulfed by the blood cell. In some preferred embodiments, CD34+ cells are removed prior to isolation of mRNA from samples using commercially available immuno-columns.

Aspects of the present invention include various methods of determining whether a sample contains cells that express CDX2 by nucleotide sequence-based molecular analysis to detect the CDX2 gene transcript. Several different methods are available for doing so including those using Polymerase Chain Reaction (PCR) technology, branched oligonucleotide technology, Northern blot technology, oligonucleotide hybridization technology, and in situ hybridization technology.

The invention relates to oligonucleotide probes and primers used in the methods of identifying the CDX2 gene transcript and to diagnostic kits which comprise such components.

The mRNA sequence-based methods for detect the CDX2 gene transcript include but are not limited to polymerase chain reaction technology, branched oligonucleotide technology, Northern and Southern blot technology, in situ hybridization technology and oligonucleotide hybridization technology.

The methods described herein are meant to exemplify how the present invention may be practiced and are not meant to limit the scope of invention. It is contemplated that other sequence-based methodology for detecting the presence of the CDX2 gene transcript in non-colorectal samples may be employed according to the invention.

A preferred method to detecting the CDX2 gene transcript in genetic material derived from non-colorectal samples uses polymerase chain reaction (PCR) technology. PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. U.S. Pat. No. 4,683,202, U.S. Pat. No. 4,683,195, U.S. Pat. No. 4,965,188 and U.S. Pat. No. 5,075,216, which are each incorporated herein by reference describe methods of performing PCR. PCR may be routinely practiced using Perkin Elmer Cetus GENE AMP RNA PCR kit, Part No. N808-0017.

PCR technology allows for the rapid generation of multiple copies of DNA sequences by providing 5' and 3' primers that hybridize to sequences present in an RNA or DNA molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the same small fragment of nucleic acid, exponential amplification of a specific double-stranded size product results. If only a single primer hybridizes to the nucleic acid fragment, linear amplification produces single-stranded products of variable length.

PCR primers can be designed routinely by those having ordinary skill in the art using sequence information. The nucleotide sequence of the CDX2 gene transcript is set forth in SEQ ID NO:1. To perform this method, RNA is extracted from cells in a sample and tested or used to make cDNA using well known methods and readily available starting materials. Those having ordinary skill in the art can readily prepare PCR primers. A set of primers generally contains two primers. When performing PCR on extracted mRNA or cDNA generated therefrom, if the CDX2 gene transcript or cDNA generated therefrom is present, multiple copies of the mRNA or cDNA will be made. If it is not present, PCR will not generate a discrete detectable product. Primers are generally 8–50 nucleotides, preferably about 15–35 nucleotides, more preferably 18–28 nucleotides, which are identical or complementary to and therefor hybridize to the CDX2 gene transcript or cDNA generated therefrom. In preferred embodiments, the primers are each 15–35 nucleotide, more preferably 18–28 nucleotide fragments of SEQ ID NO:1. The primer must hybridize to the sequence to be amplified. Typical primers are 18–28 nucleotides in length and are generally have 50% to 60% G+C composition. The entire primer is preferably complementary to the sequence it must hybridize to. Preferably, primers generate PCR products 100 base pairs to 2000 base pairs. However, it is possible to generate products of 50 to up to 10 kb and more. If mRNA is used as a template, the primers must hybridize to mRNA sequences. If cDNA is used as a template, the primers must hybridize to cDNA sequences.

The mRNA or cDNA is combined with the primers, free nucleotides and enzyme following standard PCR protocols. The mixture undergoes a series of temperature changes. If the CDX2 gene transcript or cDNA generated therefrom is present, that is, if both primers hybridize to sequences on the same molecule, the molecule comprising the primers and the intervening complementary sequences will be exponentially amplified. The amplified DNA can be easily detected by a variety of well known means. If no CDX2 gene transcript or cDNA generated therefrom is present, no PCR product will be exponentially amplified. The PCR technology therefore provides an extremely easy, straightforward and reliable method of detecting the CDX2 gene transcript in a sample.

PCR product may be detected by several well known means. The preferred method for detecting the presence of amplified DNA is to separate the PCR reaction material by gel electrophoresis and stain the gel with ethidium bromide in order to visual the amplified DNA if present. A size standard of the expected size of the amplified DNA is preferably run on the gel as a control.

In some instances, such as when unusually small amounts of RNA are recovered and only small amounts of cDNA are generated therefrom, it is desirable or necessary to perform a PCR reaction on the first PCR reaction product. That is, if difficult to detect quantities of amplified DNA are produced by the first reaction, a second PCR can be performed to make multiple copies of DNA sequences of the first amplified DNA. A nested set of primers are used in the second PCR reaction. The nested set of primers hybridize to sequences downstream of the 5' primer and upstream of the 3' primer used in the first reaction.

The present invention includes oligonucleotide which are useful as primers for performing PCR methods to amplify the CDX2 gene transcript or cDNA generated therefrom.

According to the invention, diagnostic kits can be assembled which are useful to practice methods of detecting the presence of the CDX2 gene transcript or cDNA generated therefrom in non-colorectal samples. Such diagnostic kits comprise oligonucleotide which are useful as primers for performing PCR methods. It is preferred that diagnostic kits according to the present invention comprise a container comprising a size marker to be run as a standard on a gel used to detect the presence of amplified DNA. The size marker is the same size as the DNA generated by the primers in the presence of the CDX2 gene transcript or cDNA generated therefrom. Additional components in some kits include instructions for carrying out the assay. Additionally the kit may optionally comprise depictions or photographs that represent the appearance of positive and negative results. Positive and negative controls may also be provided.

PCR assays are useful for detecting the CDX2 gene transcript in homogenized tissue samples and cells in body fluid samples. It is contemplated that PCR on the plasma portion of a fluid sample could be used to detect the CDX2 gene transcript.

Another method of determining whether a sample contains cells expressing CDX2 is by branched chain oligonucleotide hybridization analysis of mRNA extracted from a sample. Branched chain oligonucleotide hybridization may be performed as described in U.S. Pat. No. 5,597,909, U.S. Pat. No. 5,437,977 and U.S. Pat. No. 5,430,138, which are each incorporated herein by reference. Reagents may be designed following the teachings of those patents and that sequence of the CDX2 gene transcript.

Another method of determining whether a sample contains cells expressing CDX2 is by Northern Blot analysis of mRNA extracted from a non-colorectal sample. The techniques for performing Northern blot analyses are well known by those having ordinary skill in the art and are described in Sambrook, J. et al., (1989) *Molecular Cloning: A Laboratory Manual*, Cold Spring Harbor Laboratory Press, Cold Spring Harbor, N.Y. mRNA extraction, electrophoretic separation of the mRNA, blotting, probe preparation and hybridization are all well known techniques that can be routinely performed using readily available starting material.

The mRNA is extracted using poly dT columns and the material is separated by electrophoresis and, for example, transferred to nitrocellulose paper. Labeled probes made from an isolated specific fragment or fragments can be used to visualize the presence of a complementary fragment fixed to the paper. Probes useful to identify mRNA in a Northern Blot have a nucleotide sequence that is complementary to the CDX2 gene transcript. Those having ordinary skill in the art could use the sequence information in SEQ ID NO:1 to design such probes or to isolate and clone the CDX2 gene transcript or cDNA generated therefrom to be used as a probe. Such probes ate at least 15 nucleotides, preferably 30–200, more preferably 40–100 nucleotide fragments and may be the entire CDX2 gene transcript.

According to the invention, diagnostic kits can be assembled which are useful to practice methods of detecting the presence of the CDX2 gene transcript in non-colorectal samples by Northern blot analysis. Such diagnostic kits comprise oligonucleotide which are useful as probes for hybridizing to the mRNA. The probes may be radiolabeled. It is preferred that diagnostic kits according to the present invention comprise a container comprising a size marker to be run as a standard on a gel. It is preferred that diagnostic kits according to the present invention comprise a container comprising a positive control which will hybridize to the probe. Additional components in some kits include instructions for carrying out the assay. Additionally the kit may optionally comprise depictions or photographs that represent the appearance of positive and negative results.

Northern blot analysis is useful for detecting the CDX2 gene transcript in homogenized tissue samples and cells in body fluid samples. It is contemplated that PCR on the plasma portion of a fluid sample could be used to detect the CDX2 gene transcript.

Another method of detecting the presence of the CDX2 gene transcript by oligonucleotide hybridization technology. Oligonucleotide hybridization technology is well known to those having ordinary skill in the art. Briefly, detectable probes which contain a specific nucleotide sequence that will hybridize to nucleotide sequence of the CDX2 gene transcript. RNA or cDNA made from RNA from a sample is fixed, usually to filter paper or the like. The probes are added and maintained under conditions that permit hybridization only if the probes fully complement the fixed genetic material. The conditions are sufficiently stringent to wash off probes in which only a portion of the probe hybridizes to the fixed material. Detection of the probe on the washed filter indicate complementary sequences.

Probes useful in oligonucleotide assays at least 18 nucleotides of complementary DNA and may be as large as a complete complementary sequence to the CDX2 gene transcript. In some preferred embodiments the probes of the invention are 30–200 nucleotides, preferably 40–100 nucleotides.

One having ordinary skill in the art, using the sequence information disclosed in SEQ ID NO:1 can design probes useful in the invention. Hybridization conditions can be routinely optimized to minimize background signal by non-fully complementary hybridization. In some preferred embodiments, the probes are full length clones. Probes are at least 15 nucleotides, preferably 30–200, more preferably 40–100 nucleotide fragments and may be the entire CDX2 gene transcript.

The present invention includes labeled oligonucleotide which are useful as probes for performing oligonucleotide hybridization. The labeled probes of the present invention are labeled with radiolabeled nucleotides or are otherwise detectable by readily available nonradioactive detection systems.

According to the invention, diagnostic kits can be assembled which are useful to practice oligonucleotide hybridization methods of the invention. Such diagnostic kits comprise a labeled oligonucleotide which encodes portions of the CDX2 gene transcript. It is preferred that labeled probes of the oligonucleotide diagnostic kits according to the present invention are labeled with a radionucleotide. The oligonucleotide hybridization-based diagnostic kits according to the invention preferably comprise DNA samples that represent positive and negative controls. A positive control DNA sample is one that comprises a nucleic acid molecule which has a nucleotide sequence that is fully complementary to the probes of the kit such that the probes will hybridize to the molecule under assay conditions. A negative control DNA sample is one that comprises at least one nucleic acid molecule, the nucleotide sequence of which is partially complementary to the sequences of the probe of the kit. Under assay conditions, the probe will not hybridize to the negative control DNA sample. Additional components in some kits include instructions for carrying out the assay. Additionally the kit may optionally comprise depictions or photographs that represent the appearance of positive and negative results.

Oligonucleotide hybridization techniques are useful for detecting the CDX2 gene transcript in homogenized tissue samples and cells in body fluid samples. It is contemplated that PCR on the plasma portion of a fluid sample could be used to detect the CDX2 gene transcript.

The present invention relates to in vitro kits for evaluating samples of tumors to determine whether or not they are colorectal, stomach or esophageal in origin and to reagents and compositions useful to practice the same. In some embodiments of the invention, tumor samples may be isolated from individuals undergoing or recovery from surgery to remove tumors in the colorectal, stomach or esophagus, tumors in other organs or biopsy material. The tumor sample is analyzed to identify the presence or absence of the CDX2 gene transcript. Techniques such as immunohistochemistry assays may be performed to determine whether CDX2 are present in cells in the tumor sample. The presence of mRNA that encodes the CDX2 protein or cDNA generated therefrom can be determined using techniques such as in situ hybridization, immunohistochemistry and in situ ST binding assay.

In situ hybridization technology is well known by those having ordinary skill in the art. Briefly, cells are fixed and detectable probes which contain a specific nucleotide sequence are added to the fixed cells. If the cells contain complementary nucleotide sequences, the probes, which can be detected, will hybridize to them.

Probes useful in oligonucleotide assays at least 18 nucleotides of complementary DNA and may be as large as a complete complementary sequence to the CDX2 gene transcript. In some preferred embodiments the probes of the invention are 30–200 nucleotides, preferably 40–100 nucleotides.

One having ordinary skill in the art, using the sequence information set forth in SEQ ID NO:1 can design probes useful in in situ hybridization technology to identify cells that express CDX2. Probes preferably hybridizes to a nucleotide sequence that corresponds to the CDX2 gene transcript. Hybridization conditions can be routinely optimized to minimize background signal by non-fully complementary hybridization. Probes preferably hybridize to the full length CDX2 gene transcript. Probes are at least 15 nucleotides, preferably 30–200, more preferably 40–100 nucleotide fragments and may be the CDX2 gene transcript, more preferably 18–28 nucleotide fragments of the CDX2 gene transcript.

The probes are fully complementary and do not hybridize well to partially complementary sequences. For in situ hybridization according to the invention, it is preferred that the probes are detectable by fluorescence. A common procedure is to label probe with biotin-modified nucleotide and then detect with fluorescently tagged avidin. Hence, probe does not itself have to be labeled with florescent but can be subsequently detected with florescent marker.

The present invention includes labeled oligonucleotide which are useful as probes for performing oligonucleotide hybridization. That is, they are fully complementary with mRNA sequences but not genomic sequences. The labeled probes of the present invention are labeled with radiolabeled nucleotides or are otherwise detectable by readily available nonradioactive detection systems.

The present invention relates to probes useful for in situ hybridization to identify cells that express CDX2.

Cells are fixed and the probes are added to the genetic material. Probes will hybridize to the complementary nucleic acid sequences present in the sample. Using a fluorescent microscope, the probes can be visualized by their fluorescent markers.

According to the invention, diagnostic kits can be assembled which are useful to practice in situ hybridization methods of the invention are fully complementary with mRNA sequences but not genomic sequences. For example, the mRNA sequence includes different exon sequences. It is preferred that labeled probes of the in situ diagnostic kits according to the present invention are labeled with a fluorescent marker.

Immunohistochemistry techniques may be used to identify and essentially stain cells with CDX2. Such "staining" allows for analysis of metastatic migration. Anti-CDX2 antibodies such as those described above of contacted with fixed cells and the CDX2 present in the cells reacts with the antibodies. The antibodies are detectably labeled or detected using labeled second antibody or protein A to stain the cells.

The techniques described herein for evaluating tumor sections can also be used to analyze tissue sections for samples of lymph nodes as well as other tissues to identify the presence of cells that express CDX2. The samples can be prepared and "stained" to detect expression of CDX2.

Immunoassay methods may be used in the diagnosis of individuals suffering from colorectal, stomach or esophageal cancer by detecting presence of CDX2 in sample of non-colorectal tissue or body fluid from an individuals suspected of having or being susceptible to colorectal, stomach or esophageal cancer using antibodies which were produced in response to exposure to such CDX2 protein. Moreover, immunoassay methods may be used to identify individuals suffering from colorectal, stomach or esophageal cancer by detecting presence of CDX2 in sample of tumor using antibodies which were produced in response to exposure to such CDX2 protein.

The antibodies are preferably monoclonal antibodies. The antibodies are preferably raised against CDX2 made in human cells. Immunoassays are well known and there design may be routinely undertaken by those having ordinary skill in the art. Those having ordinary skill in the art can produce monoclonal antibodies which specifically bind to CDX2 and are useful in methods and kits of the invention using standard techniques and readily available starting materials. The techniques for producing monoclonal antibodies are outlined in Harlow, E. and D. Lane, (1988) *ANTIBODIES: A Laboratory Manual*, Cold Spring Harbor Laboratory, Cold Spring Harbor N.Y., which is incorporated herein by reference, provide detailed guidance for the production of hybridomas and monoclonal antibodies which specifically bind to target proteins. It is within the scope of the present invention to include Fabs, recombinant Fabs, F(Ab)2s, recombinant F(Ab)2s which specifically bind to CDX2 translation products in place of antibodies.

Briefly, CDX2 protein is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the CDX2, the hybridoma which produces them is cultured to produce a continuous supply of anti-CDX2 specific antibodies.

The antibodies are preferably monoclonal antibodies. The antibodies are preferably raised against CDX2 made in human cells.

The means to detect the presence of a protein in a test sample are routine and one having ordinary skill in the art can detect the presence or absence of a protein or an antibody using well known methods. One well known method of detecting the presence of a protein is an immunoassay. One having ordinary skill in the art can readily appreciate the multitude of ways to practice an immunoassay to detect the presence of a CDX2 protein in a sample.

According to some embodiments, immunoassays comprise allowing proteins in the sample to bind a solid phase support such as a plastic surface. Detectable antibodies are then added which selectively binding to the CDX2. Detection of the detectable antibody indicates the presence of CDX2. The detectable antibody may be a labeled or an unlabeled antibody. Unlabeled antibody may be detected using a second, labeled antibody that specifically binds to the first antibody or a second, unlabeled antibody which can be detected using labeled protein A, a protein that complexes with antibodies. Various immunoassay procedures are described in *Immunoassays for the 80's*, A. Voller et al., Eds., University Park, 1981, which is incorporated herein by reference.

Simple immunoassays may be performed in which a solid phase support is contacted with the test sample. Any proteins present in the test sample bind the solid phase support and can be detected by a specific, detectable antibody preparation. Such a technique is the essence of the dot blot, Western blot and other such similar assays.

Other immunoassays may be more complicated but actually provide excellent results. Typical and preferred immunometric assays include "forward" assays for the detection of a protein in which a first anti-protein antibody bound to a solid phase support is contacted with the test sample. After a suitable incubation period, the solid phase support is washed to remove unbound protein. A second, distinct anti-protein antibody is then added which is specific for a portion of the specific protein not recognized by the first antibody. The second antibody is preferably detectable. After a second incubation period to permit the detectable antibody to complex with the specific protein bound to the solid phase support through the first antibody, the solid phase support is washed a second time to remove the unbound detectable antibody. Alternatively, the second antibody may not be detectable. In this case, a third detectable antibody, which binds the second antibody is added to the system. This type of "forward sandwich" assay may be a simple yes/no assay to determine whether binding has occurred or may be made quantitative by comparing the amount of detectable antibody with that obtained in a control. Such "two-site" or "sandwich" assays are described by Wide, *Radioimmune Assay Method*, Kirkham, Ed., E. & S. Livingstone, Edinburgh, 1970, pp. 199–206, which is incorporated herein by reference.

Other types of immunometric assays are the so-called "simultaneous" and "reverse" assays. A simultaneous assay involves a single incubation step wherein the first antibody bound to the solid phase support, the second, detectable antibody and the test sample are added at the same time. After the incubation is completed, the solid phase support is washed to remove unbound proteins. The presence of detectable antibody associated with the solid support is then determined as it would be in a conventional "forward sandwich" assay. The simultaneous assay may also be adapted in a similar manner for the detection of antibodies in a test sample.

The "reverse" assay comprises the stepwise addition of a solution of detectable antibody to the test sample followed by an incubation period and the addition of antibody bound to a solid phase support after an additional incubation period. The solid phase support is washed in conventional fashion to remove unbound protein/antibody complexes and unreacted detectable antibody. The determination of detectable antibody associated with the solid phase support is then determined as in the "simultaneous" and "forward" assays. The reverse assay may also be adapted in a similar manner for the detection of antibodies in a test sample.

The first component of the immunometric assay may be added to nitrocellulose or other solid phase support which is capable of immobilizing proteins. The first component for determining the presence of CDX2 in a test sample is an anti-CDX2 antibody. By "solid phase support" or "support" is intended any material capable of binding proteins. Well-known solid phase supports include glass, polystyrene, polypropylene, polyethylene, dextran, nylon, amylases, natural and modified celluloses, polyacrylamides, agaroses, and magnetite. The nature of the support can be either soluble to some extent or insoluble for the purposes of the present invention. The support configuration may be spherical, as in a bead, or cylindrical, as in the inside surface of a test tube or the external surface of a rod. Alternatively, the surface may be flat such as a sheet, test strip, etc. Those skilled in the art will know many other suitable "solid phase supports" for binding proteins or will be able to ascertain the same by use of routine experimentation. A preferred solid phase support is a 96-well microtiter plate.

To detect the presence of CDX2, detectable anti-CDX2 antibodies are used. Several methods are well known for the detection of antibodies.

One method in which the antibodies can be detectably labeled is by linking the antibodies to an enzyme and subsequently using the antibodies in an enzyme immunoassay (EIA) or enzyme-linked immunosorbent assay (ELISA), such as a capture ELISA. The enzyme, when subsequently exposed to its substrate, reacts with the substrate and generates a chemical moiety which can be detected, for example, by spectrophotometric, fluorometric or visual means. Enzymes which can be used to detectably label antibodies include, but are not limited to malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. One skilled in the art would readily recognize other enzymes which may also be used.

Another method in which antibodies can be detectably labeled is through radioactive isotopes and subsequent use in a radioimmunoassay (RIA) (see, for example, Work, T. S. et al., *Laboratory Techniques and Biochemistry in Molecular Biology*, North Holland Publishing Company, N.Y., 1978, which is incorporated herein by reference). The radioactive isotope can be detected by such means as the use of a gamma counter or a scintillation counter or by autoradiography. Isotopes which are particularly useful for the purpose of the present invention are $^{3}H$, $^{125}I$, $^{131}I$, $^{35}S$, and $^{14}C$. Preferably $^{125}I$ is the isotope. One skilled in the art would readily recognize other radioisotopes which may also be used.

It is also possible to label the antibody with a fluorescent compound. When the fluorescent-labeled antibody is exposed to light of the proper wave length, its presence can be detected due to its fluorescence. Among the most commonly used fluorescent labeling compounds are fluorescein isothiocyanate, rhodamine, phycoerythrin, phycocyanin, allophycocyanin, o-phthaldehyde and fluorescamine. One skilled in the art would readily recognize other fluorescent compounds which may also be used.

Antibodies can also be detectably labeled using fluorescence-emitting metals such as $^{152}Eu$, or others of the lanthanide series. These metals can be attached to the protein-specific antibody using such metal chelating groups as diethylenetriaminepentaacetic acid (DTPA) or ethylenediamine-tetraacetic acid (EDTA). One skilled in the art would readily recognize other fluorescence-emitting metals as well as other metal chelating groups which may also be used.

Antibody can also be detectably labeled by coupling to a chemiluminescent compound. The presence of the chemiluminescent-labeled antibody is determined by detecting the presence of luminescence that arises during the course of a chemical reaction. Examples of particularly useful chemoluminescent labeling compounds are luminol, isoluminol, theromatic acridinium ester, imidazole, acridinium salt and oxalate ester. One skilled in the art would readily recognize other chemiluminescent compounds which may also be used.

Likewise, a bioluminescent compound may be used to label antibodies. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. One skilled in the art would readily recognize other bioluminescent compounds which may also be used.

Detection of the protein-specific antibody, fragment or derivative may be accomplished by a scintillation counter if, for example, the detectable label is a radioactive gamma emitter. Alternatively, detection may be accomplished by a fluorometer if, for example, the label is a fluorescent material. In the case of an enzyme label, the detection can be accomplished by colorometric methods which employ a substrate for the enzyme. Detection may also be accomplished by visual comparison of the extent of enzymatic reaction of a substrate in comparison with similarly prepared standards. One skilled in the art would readily recognize other appropriate methods of detection which may also be used.

The binding activity of a given lot of antibodies may be determined according to well known methods. Those skilled in the art will be able to determine operative and optimal assay conditions for each determination by employing routine experimentation.

Positive and negative controls may be performed in which known amounts of CDX2 proteins and no CDX2 protein, respectively, are added to assays being performed in parallel with the test assay. One skilled in the art would have the necessary knowledge to perform the appropriate controls. In addition, the kit may comprise instructions for performing the assay. Additionally the kit may optionally comprise depictions or photographs that represent the appearance of positive and negative results.

CDX2 may be produced as a reagent for positive controls routinely. One skilled in the art would appreciate the different manners in which the CDX2 protein may be produced and isolated.

Antibody composition refers to the antibody or antibodies required for the detection of the protein. For example, the antibody composition used for the detection of a CDX2 in a test sample comprises a first antibody that binds to the CDX2 as well as a second or third detectable antibody that binds the first or second antibody, respectively.

To examine a test sample for the presence of a CDX2, a standard immunometric assay such as the one described below may be performed. A first anti-CDX2 antibody, which recognizes a specific portion of CDX2, is added to a 96-well microtiter plate in a volume of buffer. The plate is incubated for a period of time sufficient for binding to occur and subsequently washed with PBS to remove unbound antibody. The plate is then blocked with a PBS/BSA solution to prevent sample proteins from non-specifically binding the microtiter plate. Test sample are subsequently added to the wells and the plate is incubated for a period of time sufficient for binding to occur. The wells are washed with PBS to remove unbound protein. Labeled anti-CDX2 antibodies, which recognize portions of CDX2 not recognized by the first antibody, are added to the wells. The plate is incubated for a period of time sufficient for binding to occur and subsequently washed with PBS to remove unbound, labeled anti-CDX2 antibody. The amount of labeled and bound anti-CDX2 antibody is subsequently determined by standard techniques.

Kits which are useful for the detection of CDX2 in a test sample comprise a container comprising anti-CDX2 antibodies and a container or containers comprising controls. Controls include one control sample which does not contain CDX2 and/or another control sample which contained the CDX2. The anti-CDX2 antibodies used in the kit are detectable such as being detectably labeled. If the detectable anti-CDX2 antibody is not labeled, it may be detected by second antibodies or protein A for example which may also be provided in some kits in separate containers. Additional components in some kits include solid support, buffer, and instructions for carrying out the assay. Additionally the kit may optionally comprise depictions or photographs that represent the appearance of positive and negative results.

The immunoassay is useful for detecting CDX2 in homogenized tissue samples and body fluid samples including the plasma portion or cells in the fluid sample.

Western Blots may be useful in assisting the diagnosis os individuals suffering from stomach or esophageal cancer by detecting presence of CDX2 of non-colorectal tissue or body fluid. Western blots may also be used to detect presence of CDX2 in sample of tumor from an individual suffering from cancer. Western blots use detectable anti-CDX2-antibodies to bind to any CDX2 present in a sample and thus indicate the presence of the receptor in the sample.

Western blot techniques, which are described in Sambrook, J. et al., (1989) *Molecular Cloning: A Laboratory Manual*, Cold Spring Harbor Laboratory Press, Cold Spring Harbor, N.Y., which is incorporated herein by reference, are similar to immunoassays with the essential difference being that prior to exposing the sample to the antibodies, the proteins in the samples are separated by gel electrophoresis and the separated proteins are then probed with antibodies. In some preferred embodiments, the matrix is an SDS-PAGE gel matrix and the separated proteins in the matrix are transferred to a carrier such as filter paper prior to probing with antibodies. Anti-CDX2 antibodies described above are useful in Western blot methods.

Generally, samples are homogenized and cells are lysed using detergent such as Triton-X. The material is then separated by the standard techniques in Sambrook, J. et al., (1989) *Molecular Cloning: A Laboratory Manual*, Cold Spring Harbor Laboratory Press, Cold Spring Harbor, N.Y.

Kits which are useful for the detection of CDX2 in a test sample by Western Blot comprise a container comprising anti-CDX2 antibodies and a container or containers comprising controls. Controls include one control sample which does not contain CDX2 and/or another control sample which contains CDX2. The anti-CDX2 antibodies used in the kit are detectable such as being detectably labeled. If the detectable anti-CDX2 antibody is not labeled, it may be detected by second antibodies or protein A for example which may also be provided in some kits in separate containers. Additional components in some kits include instructions for carrying out the assay. Additionally the kit may optionally comprise depictions or photographs that represent the appearance of positive and negative results.

Western blots are useful for detecting CDX2 in homogenized tissue samples and body fluid samples including the plasma portion or cells in the fluid sample.

Therapeutic and Prophylactic Vaccines

The invention relates to prophylactic and therapeutic vaccines for protecting individuals against metastasized colorectal cancer cells and primary and/or metastatic stomach or esophageal cancer cells and for treating individuals who are suffering from metastasized colorectal cancer cells and primary and/or metastatic stomach or esophageal cancer cells.

According to the present invention, CDX2 serves as targets against which a protective and therapeutic immune response can be induced. Specifically, vaccines are provided which induce an immune response against CDX2. The vaccines of the invention include, but are not limited to, the following vaccine technologies:

1) DNA vaccines, i.e. vaccines in which DNA that encodes at least an epitope from an CDX2 is administered to an individual's cells where the epitope is expressed and serves as a target for an immune response;

2) infectious vector mediated vaccines such as recombinant adenovirus, vaccinia, Salmonella, and BCG wherein the vector carries genetic information that encodes at least an epitope from an CDX2 protein such that when the infectious vector is administered to an individual, the epitope is expressed and serves as a target for an immune response;

3) killed or inactivated vaccines which a) comprise either killed cells or inactivated viral particles that display at least an epitope from an CDX2 protein and b) when administered to an individual serves as a target for an immune response;

4) haptenized killed or inactivated vaccines which a) comprise either killed cells or inactivated viral particles that display at least an epitope from an CDX2 protein, b) are haptenized to be more immunogenic and c) when administered to an individual serves as a target for an immune response;

5) subunit vaccines which are vaccines that include protein molecules that include at least an epitope from an CDX2 protein; and 6) haptenized subunit vaccines which are vaccines that a) include protein molecules that include at least an epitope from an CDX2 protein and b) are haptenized to be more immunogenic.

The present invention relates to administering to an individual a protein or nucleic acid molecule that comprises or encodes, respectively, an immunogenic epitope against which a therapeutic and prophylactic immune response can be induced. Such epitopes are generally at least 6–8 amino acids in length. The vaccines of the invention therefore comprise proteins which are at least, or nucleic acids which encode at least, 6–8 amino acids in length from CDX2 protein. The vaccines of the invention may comprise proteins which are at least, or nucleic acids which encode at least 10 to about 1000 amino acids in length. The vaccines of the invention may comprise proteins which are at least, or nucleic acids which encode at least, about 25 to about 500 amino acids in length. The vaccines of the invention may comprise proteins which are at least, or nucleic acids which encode at least, about 50 to about 400 amino acids in length. The vaccines of the invention may comprise proteins which are at least, or nucleic acids which encode at least, about 100 to about 300 amino acids in length.

The present invention relates to compositions for and methods of treating individuals who are known to have metastasized colorectal cancer cells and primary and/or metastatic stomach or esophageal cancer cells. Metastasized colorectal cancer and primary and/or metastatic stomach or esophageal cancer may be diagnosed by those having ordinary skill in the art using the methods described herein or art accepted clinical and laboratory pathology protocols. The present invention provides an immunotherapeutic vaccine useful to treat individuals who have been diagnosed as suffering from metastatic colorectal cancer and primary and/or metastatic stomach or esophageal cancer. The immunotherapeutic vaccines of the present invention may be administered in combination with other therapies.

The present invention relates to compositions for and methods of preventing metastatic colorectal cancer and primary and/or metastatic stomach or esophageal cancer in individual is suspected of being susceptible to colorectal, stomach or esophageal cancer. Such individuals include those whose family medical history indicates above average incidence of colorectal, stomach or esophageal cancer among family members and/or those who have already developed colorectal, stomach or esophageal cancer and have been effectively treated who therefore face a risk of relapse and recurrence. Such individuals include those which have been diagnosed as having colorectal, stomach or esophageal cancer including localized only or localized and metastasized colorectal, stomach or esophageal cancer which has been resected or otherwise treated. The vaccines of the present invention may be to susceptible individuals prophylactically to prevent and combat metastatic colorectal cancer and primary and metastatic stomach or esophageal cancer.

The invention relates to compositions which are the active components of such vaccines or required to make the active components, to methods of making such compositions including the active components, and to methods of making and using vaccines.

The amino acid and nucleotide sequences of the CDX2 is set forth as SEQ ID NO:1.

The present invention relates to recombinant vectors, including expression vectors, that comprise the CDX2 gene transcript or a fragment thereof. The present invention relates to recombinant vectors, including expression vectors that comprise nucleotide sequences that encode a CDX2 protein or a functional fragment thereof.

The present invention relates to host cells which comprise such vectors and to methods of making CDX2 protein using such recombinant cells.

The present invention relates to the isolated CDX2 gene transcript and to the isolated CDX2 proteins and to isolated antibodies specific for such protein and to hybridomas which produce such antibodies.

The present invention relates to the isolated CDX2 and functional fragments thereof. Accordingly, some aspects of the invention relate to isolated proteins that comprise at least one epitope of an CDX2.

Some aspects of the invention relate to the above described isolated proteins which are haptenized to render them more immunogenic. That is, some aspects of the invention relate to haptenized proteins that comprise at least one CDX2 epitope.

Accordingly, some aspects of the invention relate to isolated nucleic acid molecules that encode proteins that comprise at least one CDX2 epitope.

Naked DNA vaccines are described in PCT/US90/01515, which is incorporated herein by reference. Others teach the use of liposome mediated DNA transfer, DNA delivery using microprojectiles (U.S. Pat. No. 4,945,050 issued Jul. 31, 1990 to Sanford et al., which is incorporated herein by reference), and DNA delivery using electroporation. In each case, the DNA may be plasmid DNA that is produced in bacteria, isolated and administered to the animal to be treated. The plasmid DNA molecules are taken up by the cells of the animal where the sequences that encode the protein of interest are expressed. The protein thus produced provides a therapeutic or prophylactic effect on the animal.

The use of vectors including viral vectors and other means of delivering nucleic acid molecules to cells of an individual in order to produce a therapeutic and/or prophylactic immunological effect on the individual are similarly well known. Recombinant vaccines that employ vaccinia vectors are, for example, disclosed in U.S. Pat. No. 5,017,487 issued May 21, 1991 to Stunnenberg et al. which is incorporated herein by reference.

In some cases, tumor cells from the patient are killed or inactivated and administered as a vaccine product. Berd et al. May 1986 *Cancer Research* 46:2572–2577 and Berd et al May 1991 *Cancer Research* 51:2731–2734, which are incorporated herein by reference, describes the preparation and use of tumor cell based vaccine products. According to some aspects of the present invention, the methods and techniques described in Berd et al. are adapted by using colorectal, stomach or esophageal cancer cells instead of melanoma cells.

The manufacture and use of isolated translation products and fragments thereof useful for example as laboratory reagents or components of subunit vaccines are well known. One having ordinary skill in the art can isolate the CDX2 gene transcript or the specific portion thereof that encodes CDX2 or a fragment thereof. Once isolated, the nucleic acid molecule can be inserted it into an expression vector using standard techniques and readily available starting materials.

The recombinant expression vector that comprises a nucleotide sequence that encodes the nucleic acid molecule that encodes CDX2 or a fragment thereof or a protein that comprises the CDX2 or a fragment thereof. The recombinant expression vectors of the invention are useful for transforming hosts to prepare recombinant expression systems for preparing the isolated proteins of the invention.

The present invention relates to a host cell that comprises the recombinant expression vector that includes a nucleotide sequence that encodes CDX2 protein or a fragment thereof or an CDX2 or a fragment thereof. Host cells for use in well known recombinant expression systems for production of proteins are well known and readily available. Examples of host cells include bacteria cells such as *E. coli* yeast cells such as *S. cerevisiae*, insect cells such as *S. frugiperda*, non-human mammalian tissue culture cells chinese hamster ovary (CHO) cells and human tissue culture cells such as HeLa cells.

The present invention relates to a transgenic non-human mammal that comprises the recombinant expression vector that comprises a nucleic acid sequence that encodes the proteins of the invention. Transgenic non-human mammals useful to produce recombinant proteins are well known as are the expression vectors necessary and the techniques for generating transgenic animals. Generally, the transgenic animal comprises a recombinant expression vector in which the nucleotide sequence that encodes CDX2 or a fragment thereof or a protein that comprises CDX2 or a fragment thereof operably linked to a mammary cell specific promoter whereby the coding sequence is only expressed in mammary cells and the recombinant protein so expressed is recovered from the animal's milk.

In some embodiments, for example, one having ordinary skill in the art can, using well known techniques, insert such DNA molecules into a commercially available expression vector for use in well known expression systems such as those described herein.

The expression vector including the DNA that encodes a CDX2 or a functional fragment thereof or a protein that comprises a CDX2 or a functional fragment thereof is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. The methods of purifying the CDX2 or a fragment thereof or a protein that comprises the same using antibodies which specifically bind to the protein are well known. Antibodies which specifically bind to a particular protein may be used to purify the protein from natural sources using well known techniques and readily available starting materials. Such antibodies may also be used to purify the protein from material present when producing the protein by recombinant DNA methodology. The present invention relates to antibodies that bind to an epitope which is present on one or more CDX2-1 translation products or a fragment thereof or a protein that comprises the same. Antibodies that bind to an epitope which is present on the CDX2 are useful to isolate and purify the protein from both natural sources or recombinant expression systems using well known techniques such as affinity chromatography. Immunoaffinity techniques generally are described in Waldman et al. 1991 *Methods of Enzymol.* 195:391–396, which is incorporated herein by reference. Antibodies are useful to detect the presence of such protein in a sample and to determine if cells are expressing the protein. The production of antibodies and the protein structures of complete, intact antibodies, Fab fragments and $F(ab)_2$ fragments and the organization of the genetic sequences that encode such molecules are well known and are described, for example, in Harlow, E. and D. Lane (1988) *ANTIBODIES: A Laboratory Manual*, Cold Spring Harbor Laboratory, Cold Spring Harbor, N.Y. which is incorporated herein by reference.

In some embodiments of the invention, transgenic non-human animals are generated. The transgenic animals according to the invention contain nucleotides that encode CDX2 or a fragment thereof or a protein that comprises the same under the regulatory control of a mammary specific promoter. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce CDX2 or a fragment thereof or a protein that comprises the same. Preferred animals are goats and rodents, particularly rats and mice.

In addition to producing these proteins by recombinant techniques, automated peptide synthesizers may also be employed to produce CDX2 or a fragment thereof or a fragment thereof or a protein that comprises the same. Such techniques are well known to those having ordinary skill in the art and are useful if derivatives which have substitutions not provided for in DNA-encoded protein production.

In some embodiments, the protein that makes up a subunit vaccine or the cells or particles of a killed or inactivated vaccine may be haptenized to increase immunogenicity. In some cases, the haptenization is the conjugation of a larger molecular structure to CDX2 or a fragment thereof or a protein that comprises the same. In some cases, tumor cells from the patient are killed and haptenized as a means to make an effective vaccine product. In cases in which other cells, such as bacteria or eukaryotic cells which are provided with the genetic information to make and display a CDX2 or a fragment thereof or a protein that comprises the same, are killed and used as the active vaccine component, such cells are haptenized to increase immunogenicity. Haptenization is well known and can be readily performed.

Methods of haptenizing cells generally and tumor cells in particular are described in Berd et al. May 1986 *Cancer*

Research 46:2572–2577 and Berd et al May 1991 *Cancer Research* 51:2731–2734, which are incorporated herein by reference. Additional haptenization protocols are disclosed in Miller et al. 1976 *J. Immunol.* 117(5:1):1591–1526.

Haptenization compositions and methods which may be adapted to be used to prepare haptenized CDX2 immunogens according to the present invention include those described in the following U.S. Patents which are each incorporated herein by reference: U.S. Pat. No. 5,037,645 issued Aug. 6, 1991 to Strahilevitz; U.S. Pat. No. 5,112,606 issued May 12, 1992 to Shiosaka et al.; U.S. Pat. No. 4,526716 issued Jul. 2, 1985 to Stevens; U.S. Pat. No. 4,329,281 issued May 11, 1982 to Christenson et al.; and U.S. Pat. No. 4,022,878 issued May 10, 1977 to Gross. Peptide vaccines and methods of enhancing immunogenicity of peptides which may be adapted to modify CDX2 immunogens of the invention are also described in Francis et al. 1989 *Methods of Enzymol.* 178:659–676, which is incorporated herein by reference. Sad et al. 1992 *Immunolology* 76:599–603, which is incorporated herein by reference, teaches methods of making immunotherapeutic vaccines by conjugating gonadotropin releasing hormone to diphtheria toxoid. CDX2 immunogens may be similarly conjugated to produce an immunotherapeutic vaccine of the present invention. MacLean et al. 1993 *Cancer Immunol. Immunother.* 36:215–222, which is incorporated herein by reference, describes conjugation methodologies for producing immunotherapeutic vaccines which may be adaptable to produce an immunotherapeutic vaccine of the present invention. The hapten is keyhole limpet hemocyanin which may be conjugated to a CDX2 immunogen.

Vaccines according to some aspects of the invention comprise a pharmaceutically acceptable carrier in combination with a CDX2 immunogen. Pharmaceutical formulations are well known and pharmaceutical compositions comprising such proteins may be routinely formulated by one having ordinary skill in the art. Suitable pharmaceutical carriers are described in *Remington's Pharmaceutical Sciences*, A. Osol, a standard reference text in this field, which is incorporated herein by reference. The present invention relates to an injectable pharmaceutical composition that comprises a pharmaceutically acceptable carrier and a CDX2 immunogen. The CDX2 immunogen is preferably sterile and combined with a sterile pharmaceutical carrier.

In some embodiments, for example, CDX2 or a fragment thereof or a fragment thereof or a protein that comprises the same can be formulated as a solution, suspension, emulsion or lyophilized powder in association with a pharmaceutically acceptable vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

An injectable composition may comprise the CDX2 immunogen in a diluting agent such as, for example, sterile water, electrolytes/dextrose, fatty oils of vegetable origin, fatty esters, or polyols, such as propylene glycol and polyethylene glycol. The injectable must be sterile and free of pyrogens.

The vaccines of the present invention may be administered by any means that enables the immunogenic agent to be presented to the body's immune system for recognition and induction of an immunogenic response. Pharmaceutical compositions may be administered parenterally, i.e., intravenous, subcutaneous, intramuscular.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired. An amount of immunogen is delivered to induce a protective or therapeutically effective immune response. Those having ordinary skill in the art can readily determine the range and optimal dosage by routine methods.

What is claimed is:

1. A method of determining whether or not an individual has stomach cancer comprising the step of examining a sample of stomach tissue to detect the presence of CDX2 transcript wherein the presence of CDX2 transcript in a stomach sample indicates stomach cancer.

2. The method of claim 1 wherein the presence of CDX2 gene transcription product is determined by polymerase chain reaction wherein said sample is contacted with primers that selectively amplify CDX2 gene transcript of cDNA generated therefrom.

3. A method of determining whether or not an individual has esophageal cancer comprising the step of examining a sample of esophagus tissue to detect the presence of CDX2 transcript wherein the presence of CDX2 transcript in an esophageal sample indicates esophageal cancer.

4. The method of claim 3 wherein the presence of CDX2 gene transcription product is determined by polymerase chain reaction wherein said sample is contacted with primers that selectively amplify CDX2 gene transcription or cDNA generated therefrom.

5. A method of confirming the diagnosis of stomach cancer in an individual who has been diagnosed as having stomach cancer comprising the step of: examining a sample of stomach tissue from an individual who has been diagnosed as having stomach cancer to detect the presence of CDX2 transcription or translation product wherein the presence of CDX2 transcript or translation product in a stomach sample confirms the diagnosis of stomach cancer.

6. The method of claim 5 wherein the presence of CDX2 gene transcription product is determined by polymerase chain reaction wherein said sample is contacted with primers that selectively amplify CDX2 gene transcript of cDNA generated therefrom.

7. A method of confirming the diagnosis of esophageal cancer in an individual who has been diagnosed as having esophageal cancer comprising the step of examining a sample of esophagus tissue from an individual who has been diagnosed as having esophageal cancer to detect the presence of CDX2 transcript or translation product wherein the presence of CDX2 transcript or translation product in an esophageal sample confirms the diagnosis of esophageal cancer.

8. The method of claim 7 wherein the presence of CDX2 gene transcription product is determined by polymerase chain reaction wherein said sample is contacted with primers that selectively amplify CDX2 gene transcript or cDNA generated therefrom.

* * * * *